United States Patent [19]

Krsmanovic et al.

[11] Patent Number: 5,378,815
[45] Date of Patent: Jan. 3, 1995

[54] PROCESS FOR INDIRECT TARGETED IMMUNOCYTOLYSIS

[75] Inventors: Velibor Krsmanovic, Ecully, France; Jon P. Durkin, Gloucester; Jagmohan L. Bhasin, Orleans, both of Canada; Jean-Michel Biquard, Palaiseau, France; Phillip A. Macdonald; James F. Whitfield, both of Ottawa, Canada

[73] Assignees: National Research Council Canada, Ottawa, Canada; Consel National de Recherche Scientifique, Paris, France

[21] Appl. No.: 872,966

[22] Filed: Feb. 10, 1992

Related U.S. Application Data

[63] Continuation-in-part of Ser. No. 424,636, Oct. 20, 1989, abandoned.

[51] Int. Cl.$^6$ .......................................... A61K 39/385
[52] U.S. Cl. .................................. 530/405; 530/403; 530/404; 424/197.11
[58] Field of Search ............... 424/85, 8, 88, 89, 92; 530/350, 397, 398, 399, 404, 405, 408, 409, 806, 807, 403; 514/8, 21; 604/5

[56] References Cited

U.S. PATENT DOCUMENTS

| | | | |
|---|---|---|---|
| 4,268,435 | 5/1981 | Bahl | 424/88 |
| 4,384,995 | 5/1983 | Stevens | 424/88 |
| 4,440,747 | 4/1984 | Neville, Jr. et al. | 424/85.91 |
| 4,489,710 | 12/1984 | Splitler | 424/85.91 |
| 4,493,795 | 1/1985 | Nestor, Jr. et al. | 530/327 |
| 4,676,980 | 6/1987 | Segal et al. | 424/85.91 |

FOREIGN PATENT DOCUMENTS

| | | | |
|---|---|---|---|
| 0336379 | 10/1989 | European Pat. Off. | |
| 8606635 | 11/1986 | WIPO | A61K 39/385 |
| 8801176 | 2/1988 | WIPO | A61K 39/385 |

OTHER PUBLICATIONS

Krsmanovic et al (1988 Dec. 15) Biochem. Biophys. Res. Commun 157:(2):762–769.
Liu et al (1985) Proc. Natl. Acad. Sci. USA 82:8648–8652.
Ladd et al (1988) AJRIM 17:121–127.

Primary Examiner—Kay K. A. Kim
Attorney, Agent, or Firm—Sughrue, Mion, Zinn, Macpeak & Seas

[57] ABSTRACT

A process is disclosed for treating cancer by the process of indirect targeted immunocytolysis, which comprises conjugating an immunogenic sensitizing agent to a targeting agent which is capable of binding to aberrant cells, such as cancer cells in a human or animal host. The conjugate is then introduced into the body of an animal or human which has previously been actively immunized against the sensitizing agent or concomitantly treated with the appropriate antibody (passive immunization). Binding of the conjugate to the object cells occurs and is accompanied by the binding of antibodies produced against the sensitizing agent. This results in triggering of a complement cascade and/or an antibody-dependent T-cell-mediated response leading to cell destruction. Also disclosed are the novel targeting agent/sensitizing agent conjugates for use in the process. Agents comprise autocrine differentiation-inhibiting factor/toxoid conjugates.

2 Claims, 4 Drawing Sheets

A UNTREATED CELLS → UNVACCINATED MICE
B ADIF-TOXOID TREATED CELLS → VACCINATED MICE
C UNTREATED CELLS → VACCINATED MICE
D ADIF-TOXOID TREATED CELLS → UNVACCINATED MICE

INDIRECT TARGETED IMMUNOCYTOLYSIS

* THE NUMBERS IN BRACKETS ARE THE NUMBERS
OF ANIMALS IN EACH EXPERIMENTAL GROUP

FIGURE 6

* THE NUMBERS IN BRACKETS ARE THE NUMBERS OF ANIMALS IN EACH EXPERIMENTAL GROUP

PROCESS FOR INDIRECT TARGETED IMMUNOCYTOLYSIS

This application is a continuation-in-part of application Ser. No. 424,636, filed Oct. 20, 1989, now abandoned.

BACKGROUND OF THE INVENTION

This invention relates to a process of indirect targeted immunocytolysis, hereinafter referred to as ITIC, as a method of treating cancer.

DESCRIPTION OF THE RELATED ART

Significant efforts have been directed in recent years towards the development of therapeutic procedures to specifically target and destroy aberrant cells in the body which are responsible for a variety of diseases. The potential use of Paul Erlich's so called "magic bullets" in cancer therapy has been of particular interest. Briefly, these "bullets" link a molecule which specifically recognizes the target cell (the targeting agent) to a second component which is highly toxic to cells (the killing agent). Lectins, hormones and especially antibodies have been used as agents to specifically target cancer cells. They do so by recognizing and binding to specific cell surface sites and antigens which are expressed by the cancer cells, but are expressed to a lesser extent by, or are virtually absent from, most normal cells in the body. The targeting agent is conjugated (i.e. covalently linked) to a cytotoxic agent such as a radionuclide, chemotherapeutic drug, or, especially, a toxic protein. In recent years. immunotoxins (antibody-toxin conjugates) have emerged as the most promising of the various conjugates being considered for clinical use.

In a further technique, a limited kind of "hormone-withdrawal" procedure is provided by the teaching of Stevens (U.S. Pat. No. 4,384,995). According to this approach, cancer cell growth can be selectively reduced or entirely inhibited without directly killing the cancer cells by using a technique that enables a human or animal to generate antibodies to, and thus reduce the level of, a natural hormone that the cancer cells specifically need for their proliferation. In other words, this immunological procedure can be used to prevent the growth of specifically hormone-dependent cancer.

Despite encouraging initial results, many problems must be solved before antibody conjugates can be effectively used clinically to directly destroy unwanted cells. For example, a drug-antibody conjugate should clearly discriminate between tumour and normal tissues in order to selectively kill tumour cells, while leaving normal cells untouched. A number of monoclonal antibodies, raised against tumour cell-surface markers, have been conjugated to various cell-killing toxins to attach the toxins to their cellular targets. Unfortunately, these conjugates have not lived up to expectations, because they have proven to be less than effective in specifically targeting tumour cells in the body. In addition, since most monoclonal antibodies are of rodent origin, humans treated with such antibody-cytotoxin conjugates can elicit humoral or cell-mediated antibody responses that prevent repeated use of these foreign biological substances. Furthermore, the Fc portion of antibodies can bind to Fc receptors on the surface of a variety of non-targeted cells, which increases the chances of generalized, nonspecific cytotoxicity. Finally, cytotoxic agents attached to antibodies can direct these conjugates to the reticuloendothelial system of the liver which can damage that organ, although the use of deglycosylated toxins in such conjugates may mitigate this problem.

An alternative use of immunotoxins is the in vitro cleaning of cancer cells from bone marrow in autoiogous transplantation therapy. The immunotoxin is used to target and selectively eliminate cancer cells from the diseased bone marrow isolated from cancer patients. The bone marrow which has been selectively rid of cancer cells by the immunotoxin is then reinjected into the patient who in the interim has undergone radiotherapy and/or chemotherapy. In principle, these selectively "cleaned" bone marrow populations should repopulate the bone marrow with normal, non-cancerous cells.

SUMMARY OF THE INVENTION

It is an object of the present invention to provide an improved generally applicable technique for selectively targeting and then directly killing cancer cells in vivo by an antigen-antibody-triggered cytolytic mechanism which mitigates various limitations and drawbacks of the prior techniques outlined above.

The term "targeting agent" as used herein refers to any agent that modifies the growth and differentiation of a specific target cell, and includes such materials as hematopoietic differentiation-inhibiting factors, hematopoietic differentiation-inducing factors, growth factors and hormones.

The invention provides a process for indirect targeted immunocytolysis, which comprises:
  (a) conjugating an immunogenic "sensitizing agent" to a "targeting agent" (in a manner that does not impair the binding of the targeting agent to its target molecule) the purpose of which is to bind selectively to a given kind of cancer cell designated for destruction in a human or animal body and thereby to bring the coupled sensitizing agent to the target cancer cell surface;
  (b) introducing the sensitizing agent-targeting agent conjugate into the body of an animal or human (which has already been actively or passively immunized against the sensitizing agent) where the conjugate binds to the object cancer cells by the conjugate's component targeting agent and at the same time triggers the reaction of the conjugate's component sensitizing agent with ambient anti-sensitizing agent antibodies that triggers a complement cascade and/or T-cell mediated response that causes the aberrant object cells to lyse.

Another aspect of the invention provides a specific agent for use in indirect targeted immunocytolysis, which comprises a conjugate of a hematopoietic differentiation-inhibiting or differentiation-inducing agent and an immunogenic sensitizing agent.

DETAILED DESCRIPTION OF THE INVENTION

The invention provides a novel process for targeting and killing specified cancer cells in the body which is entirely different from conventional targeting and "magic bullet" or selective hormone-withdrawal strategies. In the process of the invention a targeting agent is conjugated, not to a killing agent which possesses inherent toxic activity (as conventional strategies dictate), but to an immunogenic molecule which will be referred to herein as the sensitizing agent. This sensitizing agent may be any molecule which possesses the following properties:

1) It must be immunogenic, which means that the compound, when injected into an animal or human, elicits an immune response which includes generating antibodies which recognize and specifically bind to the immunogen, i.e. the sensitizing agent;
2) It is not necessary that the sensitizing agent itself be toxic;
3) The sensitizing agent should not interfere with the ability of the targeting agent to bind to receptors on the surface of the targeted cell;
4) It is highly preferable, but not essential, that the sensitizing agent be, or cross-react with antibodies to, a compound against which most persons in the population-at-large have already been immunized. In other words, most people would already be carrying antibodies directed against the sensitizing agent. For the safest and most efficient use of ITIC, the sensitizing agent should be one of the molecules (e.g., diphtheria toxoid, pertussis toxin, tetanus toxoid) against which the population-at-large has been immunized as part of a public health program. Alternatively, the cytotoxic reaction can be triggered by injecting antibodies to the sensitizing agent shortly after administering the conjugate to a previously un-immunized person or animal.

One targeting agent, the chicken autocrine differentiation-inhibiting factor (ADIF) can be used to illustrate the principle of the ITIC invention.

In a 1987 publication we described a protein factor (discovered in 1986) that was produced and secreted by chicken LSCC HD3 cells, a chicken erythroleukemia cell line neoplastically transformed by a temperature-sensitive mutant of avian erythroblastosis virus (tsAEV). The AEV virus is capable of rapidly inducing erythroleukemia birds. The factor is actively secreted by these cells (but not normal chicken cells) into a culture medium which is totally free of protein and serum factors and consequently is significantly purified by acid precipitation and gel filtration chromatography. This partially purified protein was named ADIF (autocrine differentiation-inhibiting factor), and was found to have the following properties:

1) It weighs between 40 and 69 kDa;
2) It is a protein factor which is secreted by these virally-infected cells only under conditions in which the erbB oncogene of avian erythroblastosis virus is active (i.e. the cells are neoplastically transformed). Once the protein is secreted into the surrounding medium, it affects the cells which produce it by binding to receptors present on their surfaces (autocrine stimulation).
3) The binding of ADIF to its surface receptor inhibits the ability of the tsAEV-transformed chicken erythroleukemia cells that produce it to terminally differentiate into erythrocytes upon appropriate stimulation. When the temperature-sensitive erbB oncogene is inactivated by raising the temperature to a nonpermissive 41.5° C., these cells do not secrete ADIF and can now differentiate normally into erythrocytes in response to the differentiation hormone, erythropoietin. However, by adding partially purified ADIF to the medium of these cells at the nonpermissive 41.5° C., the differentiation response to erythropoietin is blocked and the cells continue to proliferate despite the signal to differentiate;
4) It is highly specific. The factor appears to affect erythroid differentiation by selectively targeting cells in the BFU-E (burst-forming erythroid) stage of normal erythroid cell differentiation;
5) It does not affect the proliferation of any cells tested, i.e. the protein does not have growth factor activity;
6) It is tissue-specific, but not species-specific. In addition to its action on chicken cells, ADtF also inhibits the differentiation of Friend murine erythroleukemia cells and normal BFU-E cells in murine and human primary bone marrow cultures.

Because this protein factor blocks the differentiation of the cells that produce it, it is termed autocrine differentiation-inhibiting factor (ADIF). It is apparent that ADIF activity is a key part of the mechanism by which avian erythroblastosis virus inhibits the maturation of BFU-E cells into erythrocytes in chickens. As a result of this blockage of the differentiation pathway there is a massive buildup of the numbers of these proliferating erythrocyte precursors. This ADIF-induced increase in BFU-E precursor cells is a principal factor in the developing erythroleukemia. Since chicken ADIF also inhibits human BFU-E cells it has significance as a targeting agent.

Conjugation of the above targeting agent with a sensitizing agent, such as diphtheria toxoid provides an ADIF-diphtheria toxoid conjugate which can be employed as one example to illustrate the generally applicable principles of the indirect targeted-immunocytolysis (ITIC) technique.

In its simplest form, the concept of indirect targeted-immunocytolysis (ITIC) can be stated as follows:

A sensitizing agent is coupled to a targeting agent which recognizes the particular population(s) of cells in the body selected for destruction. A good test model would be to conjugate diphtheria toxoid (inactivated diphtheria toxin) to ADIF in order to target erythroleukemia cells or BFU-E erythroid progenitors. This conjugate would then be introduced into the body (e.g. by intravenous injection) where it binds to both the target leukemia cells and circulating anti-toxoid antibodies (produced by either ACTIVE or PASSIVE immunization as explained in more detail below). The presence of the foreign toxoid-ADIF antigen on the cancer cell surface and the binding of anti-toxoid antibodies to the toxoid component of the conjugate bound to the surface of the target cell would trigger a complement cascade and/or an antibody-dependent T-cell-mediated response, either of which would destroy the cell.

Active immunization comprises vaccinating a patient with an immunogenic sensitizing agent which will trigger an immune response to the agent. In the simplest, though by no means limiting scenario, the sensitizing agent would be a compound against which the patient has been previously immunized through a universal Public Health Vaccination Program. Thus, introduction of the conjugate would trigger a prompt immune response to the sensitizing agent by an already-primed immune system. The advantage with this scenario is that the method can be carried out in one step, (i.e. the system is already primed), the likelihood of an adverse reaction has been minimised since the patient has already been successfully immunised to the sensitizing agent, and the rapidity of the therapy. In addition, and perhaps as important, since most patients that would be undergoing this therapy are cancer patients, with weakened or disabled immune response systems, they are less likely to mount an effective new primary response than a secondary response to an agent against which they have already been vaccinated.

To achieve passive immunization, sometime before or after treating a patient with the conjugate, antibodies/antiserum against the sensitizing agent is administered to the patient. This has two advantages over active immunization: 1) it greatly broadens the spectrum of molecules that can be used as sensitizing agents; and 2) administering the antibodies after the conjugate minimizes any harmful effects caused by the interaction of the antibodies with the conjugate before its targeting moiety can bind to the target cell (i.e. antibody-antigen clearing mechanisms).

As described above, the binding of ADIF to the surface of mouse, chicken or human erythroid/erythroleukemia cells prevents these cells from differentiating into erythrocytes. A partially purified ADIF preparation may be covalently coupled to diphtheria toxoid using the bifunctional reagent SPDP [N-succinimidyl 3-(2-pyridyldithio) propionate]. When added to a medium of cultured chicken erythroleukemia cells in the presence of anti-toxoid antibodies and complement (an 11-component system in blood and extracellular fluid which interacts with antigen-antibody complexes on cell surfaces to form a membrane perforating pore that lyses), the ADIF-toxoid conjugate killed up to 60% of the cells within 48 hrs. By contrast, the combination of complement and anti-toxoid antibodies alone (i.e. no ADIF-toxoid) was only minimally cytotoxic for these cells, as was ADIF-toxoid in the absence of complement and antibody. Thus, cells were killed only when all three components (ADIF-toxoid conjugate, complement and anti-toxoid antibodies) were present in the cell culture, indicating that cells were being killed by ITIC.

ITIC also works well in a partially in vivo animal model system. In this example, murine erythroleukemia cells were initially treated in culture with ADIF-toxoid to bind the conjugate to the cell surface. These cells were then injected into the peritoneal cavity of either unvaccinated DBA mice, or DBA mice which had been vaccinated against toxoid and were producing anti-toxoid antibodies. The anti-toxoid antibodies in the mice would seek out and bind to the injected cells bearing the toxoid-ADIF conjugate, and this antibody-antigen-ADIF cell complex would trigger a complement cascade, and possibly antibody-dependent cell-mediated cytotoxicity, either of which would kill cells. When compared to control experiments, about 80% of the ADIF-toxoid treated murine erythroleukemia cells injected into vaccinated animals are destroyed within 30 minutes. By contrast, ADIF-toxoid treated cells injected into unvaccinated mice, or untreated cells injected into vaccinated mice are not significantly affected. These data demonstrate the potential of ITIC as a way of targeting and killing specified cell populations in the body, without many of the disadvantages and limitations of conventional "magic bullet" strategies as described above.

Figure 5:
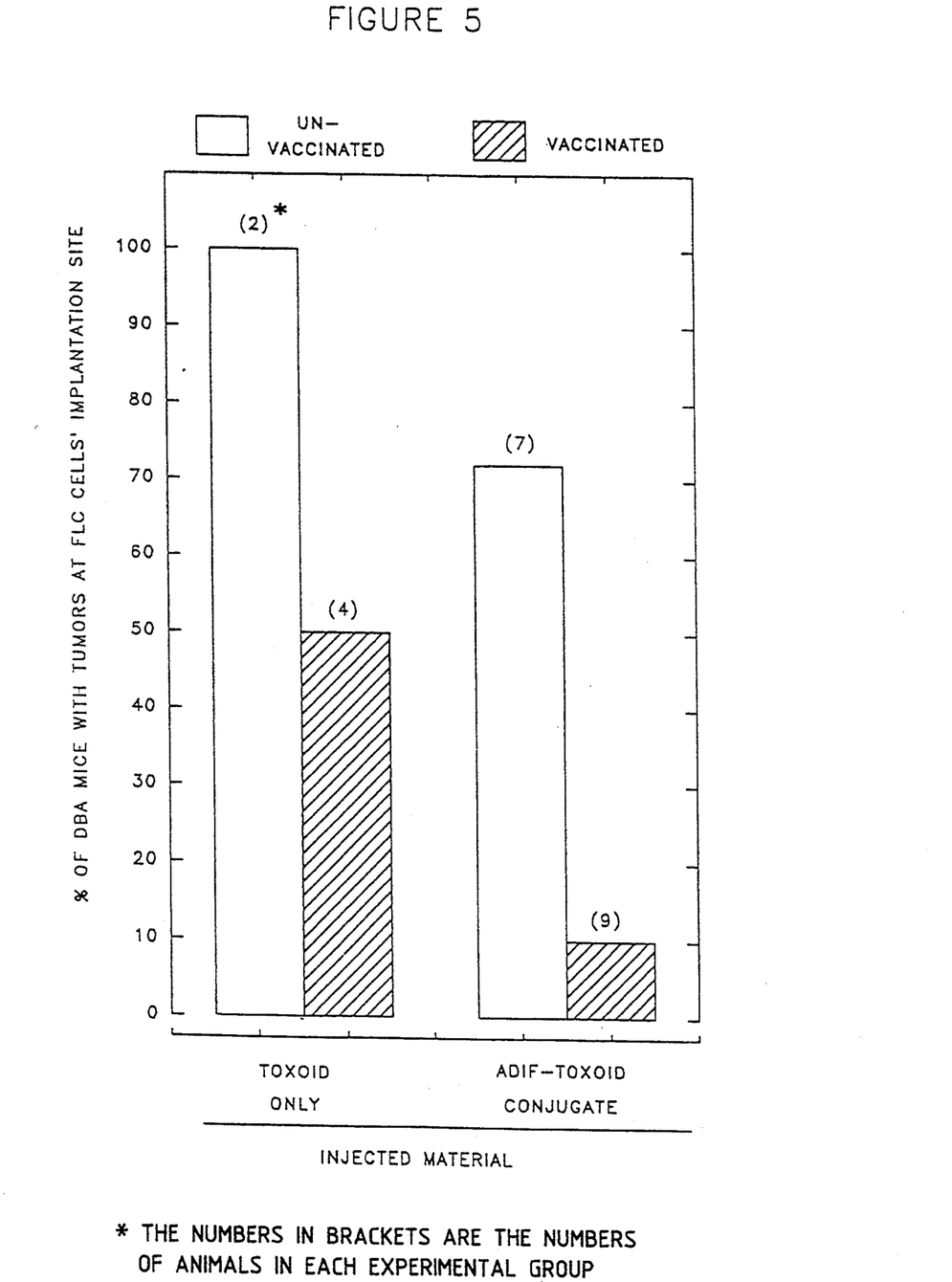
FIG. 5 shows graphically the results of ITIC testing in Example 3.

ADIF-toxoid also prevented tumour formation in a totally in vivo model when injected into toxoid-vaccinated mice containing already implanted, untreated FLC erythroleukemia cells. This was shown (Example 3; FIG. 5) by implanting $10^6$ untreated FLC cells beneath the skin in the groins of male DBA mice that had been vaccinated against diphtheria toxoid (i.e. were demonstrably producing anti-toxoid antibodies) and mice that had not been vaccinated against toxoid and then waiting for 7 days before injecting ADIF-toxoid conjugates into the tumour cell implantation site. By 3 weeks, 5 of 7 (71.4%) of unvaccinated mice had developed a tumour at the tumour cell implantation site while only 1 to 9 (11.1%) toxoid-vaccinated mice developed a tumour at the implantation site. It should be noted that in the same experiment some mice received insulin-toxoid (another targeting conjugate prepared by the same chemical coupling procedure as used to prepare the ADIF-toxoid conjugate) instead of ADIF-toxoid. 3 of the 3 unvaccinated mice developed a tumour at the implantation site but only 1 of 2 insulin-toxoid-vaccinated mice developed a tumour at the implantation site.

The technique of Indirect Targeted-Immunocytolysis (ITIC) as described herein can be used to specifically target and kill human lymphoma or leukemia cells in patients using any specific hematopoietic differentiation inhibiting or differentiation inducing factor/hormone as the "targeting agent" and any immunogen as the "sensitizing agent". More particularly ITIC can be used to specifically target and kill human erythroleukemia cells in patients using an ADIF-containing preparation (or a specific part of ADIF molecule) as the "targeting agent" and any immunogen, preferably a toxoid as the "sensitizing agent".

More broadly, ITIC can be employed to specifically target and kill human cancer cells, such as lymphoma or leukemia cells, in patients using any compound which specifically or preferentially binds to the surface of the targeted cells as the "targeting agent" and any immunogen as the "sensitizing agent". To illustrate this principle the targeting agent could be a hormone such as insulin which binds specifically to receptors on the cell surface and the sensitizing agent could again be diphtheria toxoid, widely used for human vaccination. To test this, WEHI mouse leukemia cells were exposed to insulin-toxoid complexes (prepared in the same way as ADIF-toxoid complexes) in vitro and then $10^6$ conjugate-treated cells were injected intraperitoneally almost immediately into male BALB/c mice that had been vaccinated against toxoid 32 days previously or into mice that had not been vaccinated. Twenty days later 5 of 8 (62.5%) unvaccinated mice had tumours in their peritoneal cavities, but only 1 of 8 (12.5%) toxoid-vaccinated mice had intraperitoneal tumours.

Thus, it clearly follows from these examples that ITIC can be used to specifically target and kill any designated human cancer cell population in patients using conjugates consisting of any compound which can specifically or preferentially bind to the surface of these cancer cells as the "targeting agent" and any immunogen as the "sensitizing agent".

Furthermore, since ADIF-toxoid conjugates can target and destroy erythroleukemia cells both in vitro and in vivo they could be used in an alternative strategy for autologous transplantation therapy in which immunotoxins have been traditionally used to target and eliminate cancer cells, but not normal stem cells, from the cancerous bone marrow isolated from patients. The immunotoxin-treated bone marrow cell populations are then reinjected into the patient who, in the interim, has been irradiated or chemically treated to destroy all (normal and cancerous) bone marrow cells. In theory, these "cleaned" bone marrow cells containing non-cancerous stem cells will repopulate the bone marrow with only normal, non-cancerous cells. In principle, ITIC could effectively replace the requirement for immunotoxins in this procedure by using a targeting agent that binds and kills cancer cells but not the repopulating stem cells. Upon reinjection of the ITIC-"cleaned" cell populations into the patient (who has undergone radiotherapy/chemotherapy) ITIC would be continued, now in vivo, in order to ensure the complete elimination of the cancer cells.

DESCRIPTION OF THE PREFERRED EMBODIMENTS

Experimental details will now be given by way of example of cell culture studies and animal studies using ITIC. In the accompanying drawings.

EXAMPLE 1

Figure 1:
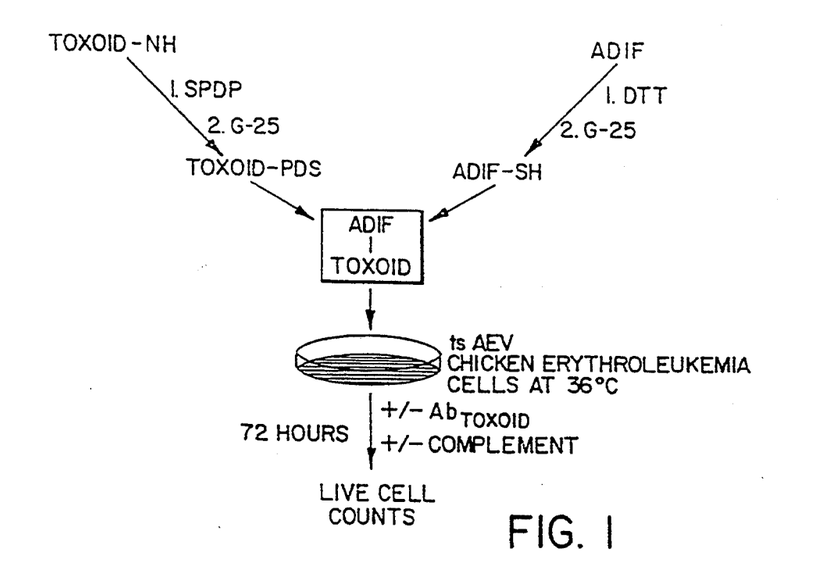
FIG. 1 shows schematically the technique of protein:protein conjugation for chicken ADIF and diphtheria toxoid.

Stock cultures of chicken erythroleukemia LSCC HD3 cells were maintained in a complete medium consisting of 90% MEM, 8% decomplemented fetal bovine serum and 2% decomplemented normal chicken serum, as described in Krsmanovic, V., Morardet, N., Biquard, J. M., Mouchirout, G., Fasciotto, B., Ristic, A., Parmentier, Blanchet, J. P., Kanazir, D., Durkin, J. P., and Whitfield, J. F., Autocrine Differentiation-Inhibiting Factor (ADIF) from Chicken Erythroleukemia Cells Acts on Human and Mouse Early BFU-E Erythroid Progenitors, *Biochem. Biophys.Res. Commun.*, 157,762,1988. Chicken ADIF, partially purified by P-60 gel filtration chromatography as described in Fasciotto, B., Kanazir, D., Durkin, J. P., Whitfield, J. F., and Krsmanovic, V., AEV-Transformed Chicken Erythroid Cells Secrete Autocrine Factors Which Promote Soft Agar Growth and Block Erythroleukemia Cell Differentiation. *Biochem. Biophys. Res. Commun.*, 143,775, 1987, was conjugated to diphtheria toxoid (Connaught Laboratories, Toronto, Canada) through the heterobifunctional reagent, SPDP (Pharamacia Ltd., Uppsala, Sweden). Protein:protein conjugation was accomplished using the standard method supplied with the SPDP reagent, and which is summarized in FIG. 1.

For individual experiments, cells were plated in 24-well dishes at 250,000 cells per well in 0.2 ml of complete medium. The cells in some wells were treated with either the ADIF-Toxoid conjugate (20 $\mu$l; 3.4 $\mu$g protein) in complete medium, ADIF alone (1.7 $\mu$g protein) in complete medium, or left untreated in complete medium alone. The cultures were incubated for 30 min at 37° C. to allow binding of ADIF (or ADIF-toxoid) to the cell surface receptors. Decomplemented toxoid antiserum (50 $\mu$l of a 1:10 dilution), raised in DBA/mice as described in Example 2, was then added to some cultures for 30 min at 37° C., and this was followed by the addition of guinea pig complement (25 $\mu$l) for the next 15 min at 37° C. The volume of each well was then adjusted to 1 ml with the complete medium (described above) and the cultures were incubated for 72 hours at 37° C. at which time the numbers of live cells was determined by trypan blue exclusion.

Figure 2:
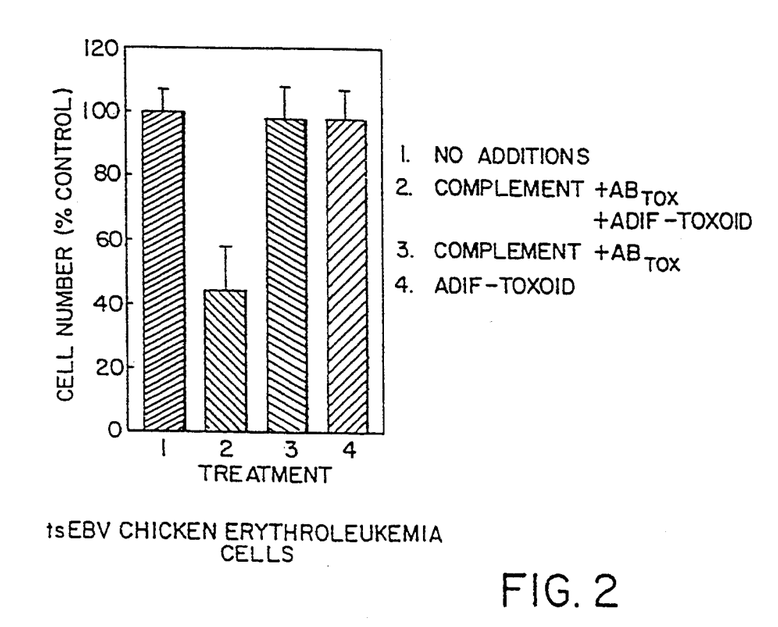
FIG. 2 shows graphically the results of the cell culture experiments of Example 1.

The results of the experiments are shown in FIG. 2. The values shown in FIG. 2 are the means +/−SEM of 4 cultures normalized to the control value. Treatments were as follows:

Treatment 1: control cultures containing no additions;

Treatment 2: Cultures treated with all of the components of ITIC (ADIF-toxoid, anti-toxoid antibody, complement) were maximally affected in that cell numbers dropped about 60% when compared to control cultures;

Treatment 3: Cultures were not adversely affected when treated with anti-toxoid antibodies and complement in the absence of ADIF-toxoid;

Treatment 4: Cultures were not adversely affected when treated with the ADIF-toxoid conjugate in the absence of toxoid antibodies and complement;

Data not shown: Incubating cells in the presence of unconjugated ADIF or toxoid in the presence of complement and anti-toxoid antibodies had only a minimal effect on cell numbers when compared to control cultures.

Thus, it can be concluded that cell numbers were reduced (i.e., cells were destroyed) only when all components of ITIC were included in the cell culture medium.

EXAMPLE 2.

Male DBA mice (6 to 8 weeks old) were housed under conventional conditions in plastic solid bottom cages with filter bonnets. Food and water was provided ad.libitum.

Mice, without detectable antibodies to diphtheria toxoid, were immunized subcutaneously with 150 $\mu$g of diphtheria toxoid in 100 $\mu$l of buffered saline on days 1,21,and 32. The first dose was emulsified in an equal volume of Freund's incomplete adjuvant and subsequent doses were in buffered saline. Ten days after the last injection the antibody response of each mouse was determined by the Ouchterlony gel diffusion test. ITIC experiments were carried out 10 days after the last injection or 10 days after boosting the animals with an additional 150 $\mu$g of diphtheria toxoid, administered subcutaneously.

Stock cultures of Friend murine erythroleukemia cells (FLC) were maintained in a complete medium consisting of 90% RPMI and 10% fetal bovine serum. Chicken ADIF was conjugated to toxoid as described in Example 1.

For individual experiments, cells were plated in 24-well dishes at 250,000 cells per well in 0.2 ml of serum-free RPMI medium. The cells in some wells were immediately treated with either the ADIF-toxoid conjugate (20 $\mu$l; 3.4 $\mu$g protein) in RPMI medium, unconjugated ADIF or toxoid alone in RPMI medium, or RPMI medium alone. The cultures were incubated for 30 min at 37° C. to allow binding of ADIF (or ADIF-toxoid) to the cell surface receptors, and they were then immediately injected into mice.

Figure 3:
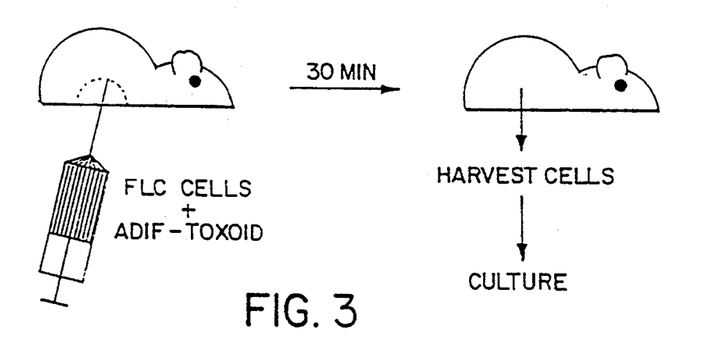
FIG. 3 shows diagrammatically the experimental strategy described in Example 2.

The experimental strategy, as shown in FIG. 3, was;
(a) injection of untreated Friend leukemia cells, or FLC cells pretreated with either ADIF, Toxoid or the ADIF-toxoid conjugate into the peritoneal cavities of the toxoid-immunized and non-immunized mice, (b) recovery of cells from the peritoneal cavity 30 minutes after initial injection, (c) demonstration of the viability of the recovered FLC cells, and (d) determination of surviving FLC cells to differentiate into hemoglobin-producing cells upon stimulation.

A more detailed description of each of these procedures follows:

(a) Groups of 5 vaccinated or non-vaccinated mice were anesthetized by an intramuscular injection of 0.15 ml of a xylazine/ketamine mixture which was sufficient to maintain anesthesia for 45 to 60 minutes. 0.2 ml of cell suspension (250,000 cells) in RPMI was injected into the peritoneal cavity of the mice which were then placed on their backs in plastic cages lined with cheese cloth. During the 30 minutes incubation, the mice were covered with a layer of cheese cloth to avoid hypothermic shock.

(b) Following the 30 min incubation, 4 ml of serum-free RPMI was injected intraperitoneally into the animals and after gentle manipulation of the abdomen wall, the fluid containing the FLC cells and other peritoneal cells was carefully withdrawn.

(c) 0.25 mls of each of the FLC-containing peritoneal fluids were plated in 24-well tissue culture plates containing 0.75 ml of RPMI containing 10% fetal bovine serum. The cultures were incubated at 37° C. and cell numbers and viabilities were determined 0,24,48,72 and 120 hours later by counting trypan blue stained preparations in a hemacytometer.

(d) The ability of the viable FLC cells to differentiate into hemoglobin-producing cells after passing through the animal was determined by treating 24-hour cell cultures with 2% DMSO. The proportion of hemoglobin-producing cells was determined 5 days later by the standard benzidine method described by Krsmanovic et al (see Example 1 above).

Figure 4:
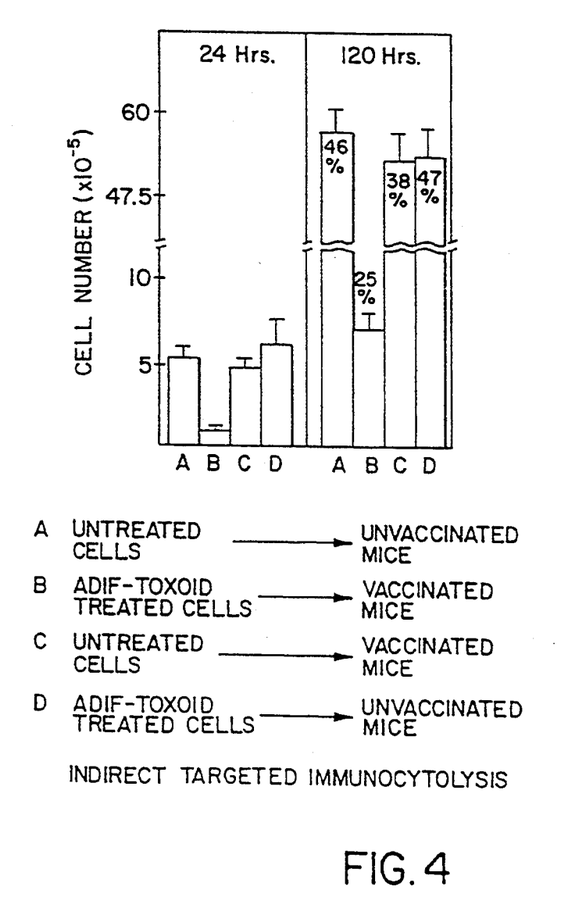
FIG. 4 shows graphically the results of ITIC testing in Example 2.

The results obtained were as follows. Microscopic examination of the peritoneal lavage from various groups of mice revealed a heterogeneous population of cells which could be classified as either large cells (peritoneal macrophages) or medium cells (peritoneal lymphocytes and Friend Leukemia cells). The FLC cells were easily identified by their granular cytoplasm, whereas the peritoneal lymphocytes were uniformly round with clearly a non-granular cytoplasm. Both the large cells and peritoneal lymphocytes did not grow in RPMI. In fact, these cells died (as judged by trypan blue staining) within 24 hours of being placed into cell culture (data not shown). Thus, any increase in the number of suspended cells upon incubation in complete RPMI medium must have resulted from the proliferation of FLC cells. The data presented in FIG. 4 shows the numbers of viable FLC cells 24 hours and 120 hours after recovery from the peritoneal cavity of mice.

After 24 hours in culture, the number of ADIF-toxoid-treated FLC cells recovered from the peritoneal cavities of toxoid-immunized mice was only 15–20% ($0.85 \times 10^5$ cells; FIG. 4, lane B) of the number of ADIF-toxoid-treated FLC cells which were recovered from the peritoneal cavities of non-immunized mice ($6.0 \times 10^5$ cells; FIG. 4, lane D). These numbers were also significantly lower than the numbers of untreated FLC cells which were recovered from the peritoneal cavities of either immunized or non-immunized mice (FIG. 4, lanes A and C). After 120 hours in culture it became clear that the growth and viability of ADIF toxoid treated FLC cells recovered from immunized mice was again significantly lower than cells recovered from non-immunized mice or untreated FLC cells recovered from either vaccinated or non-vaccinated mice. Only 25% of the FLC cells treated with ADIF-toxoid and recovered from immunized mice were able to differentiate into hemoglobin-producing cells in response to DMSO, as compared to 47% of similar cells recovered from non-immunized mice. The percentage differentiation of untreated FLC cells recovered from immunized and non-immunized mice was 38 and 46%, respectively, after DMSO treatment.

EXAMPLE 3

FLC (Friend erythroleukemia) mouse cells were cultured as in Example 2. $10^6$ of these cells were implanted beneath the skin in the groins of male DBA mice which had been vaccinated 32 days previously against diphtheria toxin and were actively producing anti-toxoid antibodies (as demonstrated by standard procedures) or were not vaccinated against the toxoid (see Example 2). Seven days later the vaccinated and unvaccinated animals received one injection of either diphtheria toxoid (37 $\mu$g) or ADIF-toxoid (1 $\mu$g of ADIF-37 $\mu$g of toxoid) at the site of FLC cell implantation. By 21 days far fewer mice that had been toxoid-vaccinated and received ADIF-toxoid conjugates had a tumour at the cancer cell implantation site than unvaccinated animals that had received toxoid alone (FIG. 5). However, toxoid alone had some ability to stop tumour growth in toxoid-vaccinated mice, but it was much less effective than ADIF-toxoid in toxoid-vaccinated mice (FIG. 5). It may be concluded that ADIF-toxoid conjugates can target and kill implanted, ADIF-binding FLC cancer cells in a toxoid-vaccinated animal as required by the ITIC concept.

EXAMPLE 4

Figure 6:
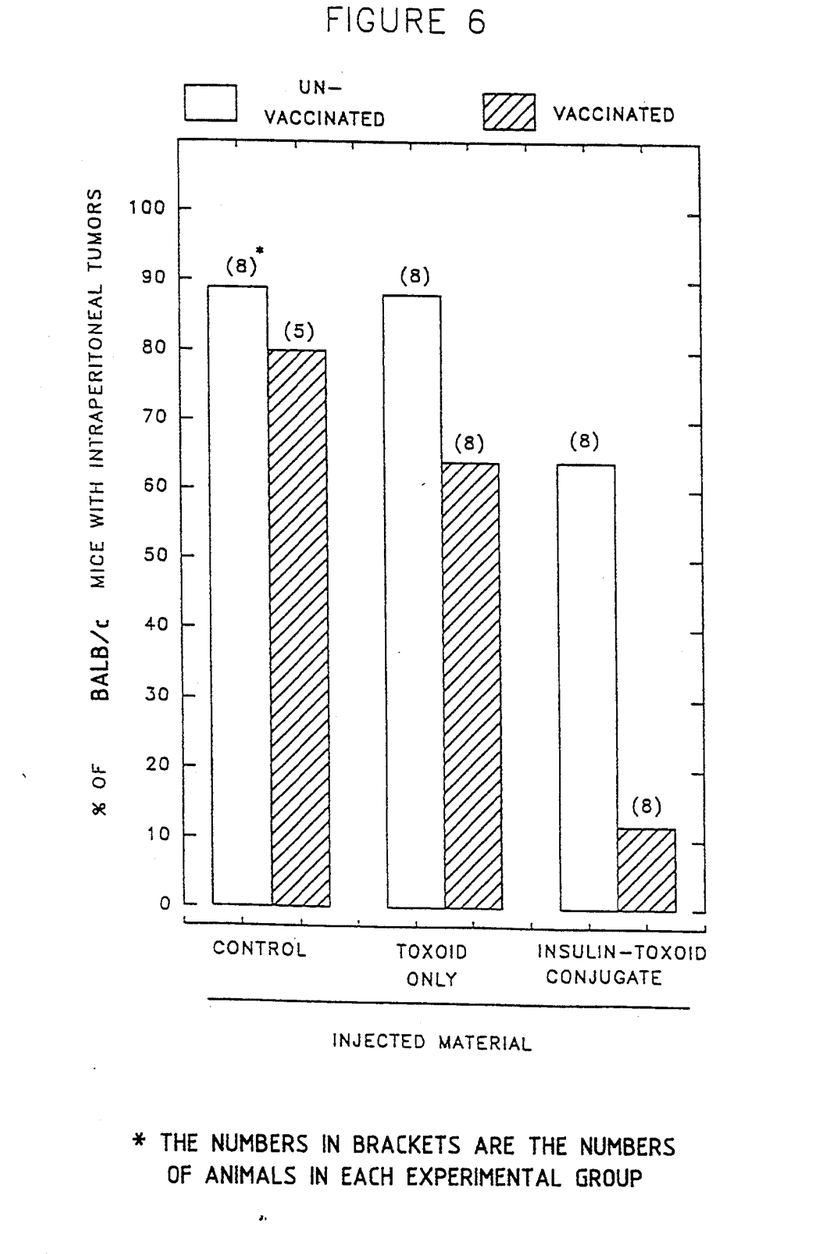
FIG. 6 show graphically the results of ITIC testing in Example 4.

CRL 1751 WEHI mouse leukemia cells were cultured in the same way as FLC cells. WEHI cells were exposed to insulin-diphtheria toxoid conjugates (20 $\mu$l per culture well; 3.5 $\mu$g of protein per well; prepared using the same coupling chemistry that was used to conjugate ADIF with toxoid) in vitro (see Example 1). Almost immediately after being exposed to the conjugate, $10^6$ cells were injected into the peritoneal cavities of male BALB/c mice which had been vaccinated against toxoid 32 days previously and were producing anti-toxoid antibodies (see Example 2) or had been vaccinated against toxoid. At 20 days all of the animals were sacrificed and examined for intraperitoneal tumours. Toxoid alone reduced intraperitoneal tumour formation, but in confirmation of the ITIC concept the insulin-toxoid conjugate was by far the more effective in preventing the formation of intraperitoneal tumours, as seen in FIG. 6.

Thus, it may be concluded that only those FLC cells which had been exposed to all of the components of ITIC (i.e., ADIF-toxoid pretreatment followed by toxoid-antibody and complement in the animal) were preferentially killed when compared to all control conditions. Thus, ITIC was responsible for cytolysis.

It will be clear to anyone skilled in the art that many other kinds of conjugate can be made to treat other types of cancer. Thus it will be appreciated that numerous changes and modifications can be made in the embodiments of the invention described above without departing from the scope of the invention. Accordingly, the foregoing description is to be construed as illustrative and not in a limiting sense, the scope of the invention being defined solely by the appended claims.

We claim:

1. A conjugate for treating leukemia or lymphoma comprising an immunogenic sensitizing agent and a targeting agent, wherein said targeting agent is an autocrine differentiation-inhibiting factor and said sensitizing agent is a toxoid.

2. A conjugate according to claim 1, wherein said targeting agent is chicken autocrine differentiation-inhibiting factor and said sensitizing agent is diphtheria toxoid.

* * * * *